United States Patent
Russell et al.

[11] Patent Number: 5,895,629
[45] Date of Patent: Apr. 20, 1999

[54] RING OSCILLATOR BASED CHEMICAL SENSOR

[76] Inventors: Stephen D. Russell, 4561 Osprey St., San Diego, Calif. 92107; Shannon D. Kasa, 3963 San Martine Way, San Diego, Calif. 92130; Howard W. Walker, 4544 Granger St., San Diego, Calif. 92107

[21] Appl. No.: 08/977,720

[22] Filed: Nov. 25, 1997

[51] Int. Cl.[6] .................................................. G01N 25/32
[52] U.S. Cl. ........................ 422/94; 422/95; 340/633
[58] Field of Search .................................. 422/93, 94, 98, 422/82.12, 90, 95; 436/151, 152; 331/65, 66; 340/632, 633, 634; 327/437

[56] References Cited

U.S. PATENT DOCUMENTS

| | | | |
|---|---|---|---|
| 3,895,912 | 7/1975 | Naumann | 422/93 |
| 4,227,182 | 10/1980 | Ogasawara et al. | 340/870.37 |
| 4,368,480 | 1/1983 | Senturia | 257/253 |
| 4,549,427 | 10/1985 | Kolesar, Jr. | 422/98 X |
| 4,596,697 | 6/1986 | Ballato | 422/98 |
| 5,281,836 | 1/1994 | Mosser et al. | 257/254 |
| 5,309,117 | 5/1994 | Cadotte, Jr. et al. | 331/66 |
| 5,642,098 | 6/1997 | Santa Maria et al. | 340/618 |
| 5,722,290 | 3/1998 | Kronberg | 73/304 C |

FOREIGN PATENT DOCUMENTS 0142481  5/1985  European Pat. Off. .

*Primary Examiner*—Jeffrey Snay
*Attorney, Agent, or Firm*—Peter J. Van Bergen

[57] ABSTRACT

A chemical sensor couples a material that changes temperature in response to a chemical condition with an oscillator. The oscillator is coupled to the material to detect the change in temperature in the material so that the frequency of the oscillator changes in correspondence with the change in temperature as an indication of the chemical condition.

15 Claims, 2 Drawing Sheets

RING OSCILLATOR BASED CHEMICAL SENSOR

STATEMENT OF GOVERNMENT INTEREST

This invention was made with Government support under contract N66001-94-D-0017 awarded by the Space and Naval Warfare System Center, San Diego, Calif. The Government has certain rights in this invention.

FIELD OF THE INVENTION

The invention relates generally to sensing devices, and more particularly to a chemical sensor that incorporates an oscillator and an active material as part thereof.

BACKGROUND OF THE INVENTION

Microelectronic chemical sensors are desirable for a variety of Naval and commercial applications since they present a small-size, light-weight and low cost alternative to conventional chemical sensors. Chemical sensors are used in a variety of applications that include shipboard and ashore effluent control, littoral warfare, intelligence gathering and manning reduction, as well as a variety of bio-medical applications. Furthermore, if sensors can be made using microelectronics fabrication, they can potentially take advantage of monolithic integration of multiple sensors with associated discrimination, amplification and logic circuitry.

SUMMARY OF THE INVENTION

Accordingly, it is an object of the present invention to provide a chemical sensor construction adaptable to a variety of applications.

Another object of the present invention is to provide a chemical sensor construction that can exploit the advantages offered by microelectronics fabrication.

Yet another object of the present invention is to provide a chemical sensor construction that contains a monolithically integrated sensor portion, reference portion and processor portion by microelectronics fabrication.

Other objects and advantages of the present invention will become more obvious hereinafter in the specification and drawings.

In accordance with the present invention, a chemical sensor couples a material that changes temperature in response to a chemical condition with an oscillator. More specifically, the oscillator is coupled to the material in one of a variety of disclosed ways to detect the change in temperature in the material. The frequency of the oscillator changes in correspondence with the change in temperature in the material as an indication of the chemical condition. In its preferred embodiments, the material is monolithically integrated with a ring oscillator.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

The present invention couples the frequency sensitivity of an oscillator with the chemical sensitivity of an active material that reacts with its changing environment to produce a corresponding temperature change of the active material. In general, the active material is coupled to the oscillator in such a way that the frequency of oscillation of the oscillator changes with the changing local temperature of the material. The oscillator can be any of a variety of commercially available oscillators having a frequency of oscillation that is dependent on either resistive loading or the temperature of its environment. Oscillators of various types, which may be modified to accommodate the teachings herein, may be obtained from Hewlett Packard of Palo Alto Calif., Ecliptek Corporation of Costa Mesa Calif., SaRonix of Palo Alto Calif., Abracon of Viejo Calif., Vectron Technologies of Hudson N.H., ILSI America of Kirkland Wash., Fujitsu of Japan, and many other vendors. In the preferred embodiment, the oscillator is comprised of an odd number of microelectronic inverters connected in series. Such an oscillator is commonly known as a ring oscillator. Ring oscillators can be monolithically integrated with analog or digital circuitry to provide for desired signal processing. Monolithic integration implies that the ring oscillators and the associated processing circuitry are simultaneously fabricated using microelectronic fabrication techniques on the same substrate.

The active material in the present invention reacts to a chemical condition, e.g. the presence of a chemical or biological agent, to be monitored or measured such that the material's temperature changes by such reaction. The active material participates directly, or indirectly as a catalyst, in exothermic or endothermic chemical reactions. In a preferred embodiment, the active material is a catalyst, i.e. a material that accelerates chemical reactions without itself being substantially consumed. Examples of non-living cell catalysts include, but are not limited to, platinum, aluminum oxide, cobalt, nickel, iron, silver, chromic oxide, aluminum chloride, magnesium dioxide, molybdenum oxide, vanadium pentoxide and copper salts.

Figure 1A:
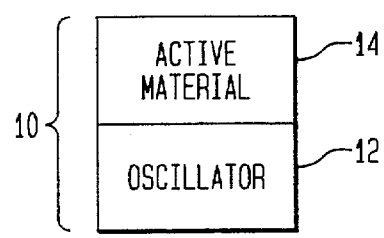
FIG. 1A is a schematic diagram of an embodiment of a chemical sensor of the present invention in which an active material is in contact with an oscillator.
Figure 1B:
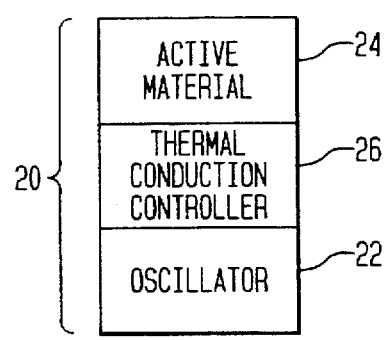
FIG. 1B is a schematic diagram of another embodiment of a chemical sensor of the present invention in which a thermal conduction controller is used to couple the active material to the oscillator.
Figure 1C:
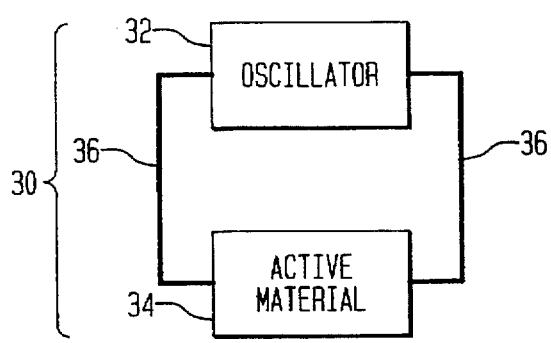
FIG. 1C is a schematic diagram of yet another embodiment of a chemical sensor of the present invention in which the active material is coupled to the oscillator as a resistive load.

Referring now to the drawings, and more particularly to FIGS. 1A–1C, the sensing device of the present invention is shown schematically in three embodiments thereof. In FIG. 1A, chemical sensor 10 includes an oscillator 12 in physical contact with an active material 14 that reacts to the chemical condition being sensed in such a way that its temperature changes. For example, this may occur when the active material, while in the presence of an appropriate environment, undergoes an exothermic or endothermic chemical reaction. A specific example is the exothermic catalytic oxidation of platinum that occurs above about 200° C. which occurs with the presence of oxygen. A suitable oscillator 12 is a Complementary-Metal-Oxide-Semiconductor (CMOS) microelectronic ring oscillator circuit, the construction of which is known in the art.

By way of example, the frequency of a ring oscillator having 71 inverter stages with nominally 1.25 micron gate lengths at 5 volt bias and fabricated in silicon-on-sapphire (SOS) changes by approximately 100 kHz per degree at room temperature. Utilizing such a high degree of resolution, chemical sensor 10 can be extremely sensitive to even small changes in a condition being monitored or measured such as detecting trace amounts of chemical or biological agents. One example of chemical sensor 10 is a combustible gas sensor where active material 14 could be a catalytic platinum layer in contact with oscillator 12. Combustible gases are catalytically oxidized at the surface of the platinum. The heat released by the exothermic reaction causes local heating of oscillator 12 which then changes its frequency of oscillation as an indication of the sensed condition.

Another example of chemical sensor 10 is an enzyme detector where active material 14 is an enzyme, i.e., a living cell catalyst, in the form of an enzyme-containing film immobilized on oscillator 12. For instance, glucose in a liquid media could be detected if the enzyme-containing film were glucose oxidase immobilized on the ring oscillator. Other examples of enzymes that may be immobilized on oscillator 12 include, but are not limited to, cholinesterase, urease, ribonuclease, cellulase, invertase, protease, rennin, pepsin, lipase, maltase, carboxylase, amylase, trypsin, and zymase.

In FIG. 1B, chemical sensor 20 includes an oscillator 22 and an active material 24 with a thermal conduction controller 26 interposed therebetween. Oscillator 22 is similar to oscillator 12 and active material 24 is similar to active material 14. Thermal conduction controller 26 can either improve or reduce the thermal conductivity between active material 24 and oscillator 22. Thermal conduction controller 26 can be selected to exhibit high thermal conductivity to efficiently conduct thermal energy to oscillator 22 to reduce response time of the sensing device. In other applications, thermal conduction controller 26 can be selected to exhibit low thermal conductivity to partially isolate active material 24 and reduce the response time or reduce heat loss to the substrate containing oscillator 22. The selection of the properties of thermal conduction controller 26 can therefore be made to meet the requirements of an application.

Figure 2:
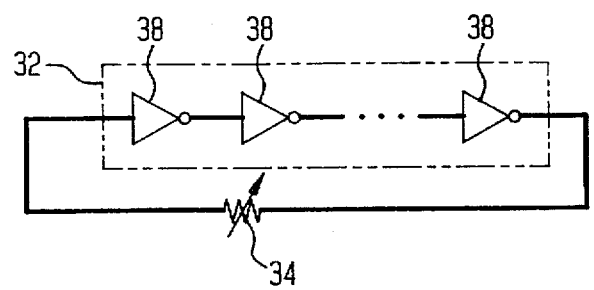
FIG. 2 is an electrical circuit schematic of the chemical sensor shown schematically in FIG. 1C.

In FIG. 1C, chemical sensor 30 includes an oscillator 32 and an active material 34 coupled to oscillator 32 as a load via leads 36. As with previous embodiments, active material 34 is a material that changes temperature in response to a sensed condition, such as the presence of chemical or biological agents, by participating directly or indirectly in a chemical reaction. However, in this embodiment, active material 34 serves as a variable resistance load where resistance changes with the temperature of active material 34. To accurately detect subtle resistive changes in active material 34, oscillator 32 is a ring oscillator and leads 36 are electrically configured to connect active material 34 in series with the chain of inverters comprising such a ring oscillator. This is shown in the electrical circuit schematic of FIG. 2 which details a preferred circuit construction of the embodiment shown in FIG. 1C. In FIG. 2, oscillator 32 is a ring oscillator having an odd number of inverters 38 which are operably coupled by a serial connection via leads 36 to active material 34 designated by a variable resistance. As the temperature and resistance of active material 34 changes in response to a sensed condition, the increase (or decrease) in its resistance causes a change in the frequency of ring oscillator 32.

Figure 3A:
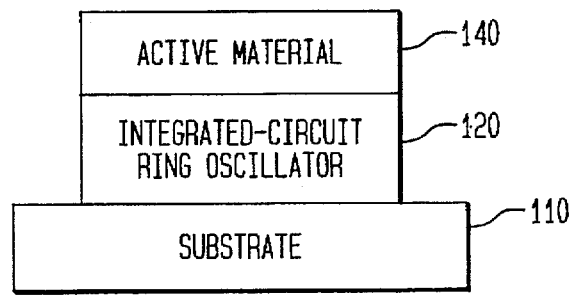
FIG. 3A is a microelectronics model of the chemical sensor shown schematically in FIG. 1A.

Due to the inherent advantages afforded by microelectronic fabrications, the present invention benefits from being fabricated as a microelectronics package. Accordingly, each of the above-described embodiments depicted in FIGS. 1A–1C is depicted as a microelectronics model in FIGS. 3A–3C, respectively. In FIG. 3A, a substrate 110 (e.g., containing semiconductors such as silicon, germanium, silicon carbide, gallium arsenide, gallium aluminum arsenide, indium phosphide, silicon-on-sapphire (SOS), silicon-on-insulator (SOI), semiconductor alloys, or superconductors such as yttria barium copper oxide (YBCO) and the like) supports an integrated-circuit oscillator 120 having active material 140 deposited thereon. Note than an electrically insulating dielectric layer (not shown) could be interposed between oscillator 120 and active material 140 if needed. Integrated-circuit oscillator 120 can be fabricated from any semiconductor or superconductor materials. For many applications, a silicon on sapphire (SOS) ring oscillator may be preferred for substrate 110/oscillator 120 where the oscillator in monolithically integrated in the silicon layer. An advantage of this embodiment is that SOS can operate at high temperatures thereby eliminating the need to thermally isolate the sensing device. Furthermore, passivation of the backside of the sensing device against undesirable chemical effects is inherently included in SOS technology. A protective passivation layer inhibits the diffusion of unwanted impurities into the device which improves the lifetime and performance of a sensing device operating in harsh environments. Therefore, the use of SOS simplifies the packaging requirements of the ultimately formed sensing device.

Figure 3B:
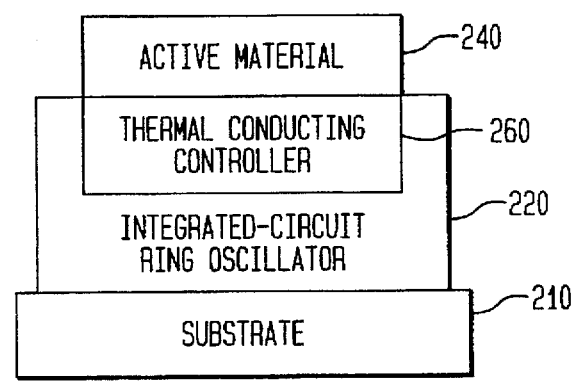
FIG. 3B is a microelectronics model of the chemical sensor shown schematically in FIG. 1B.

The microelectronics model depicted in FIG. 3B is similar to that in FIG. 3A except that a thermal conduction controller 260 is interposed between oscillator 220 and active material 240. For example, if thermal conduction is to be reduced, controller 260 represents, for example, a vacuum or partial vacuum, air, or a layer of low thermal conductivity material. Examples of materials with low thermal conductivity include, but are not limited to, silicon dioxide, silicon nitride, silicon oxynitride, alumina and aluminum nitride. If for some reason active material 240 could not be put in contact with oscillator 220 but good thermal coupling is needed, controller 260 could be a good thermal conductor. Examples of materials with high thermal conductivity include, but are not limited to, metals such as aluminum, copper, titanium, platinum and tin; metallic alloys such as titanium silicide and platinum silicide; semiconductors such as crystalline, polycrystalline or amorphous forms of silicon, germanium, silicon carbide, diamond, gallium arsenide, indium phosphide and their semiconductor alloys; and thermally conductive composites such as silver paste and thermally conductive grease (e.g., Apiezon® N-grease or Apiezon® H-grease available from MBI Materials, Ltd. of Manchester, UK).

Figure 3C:
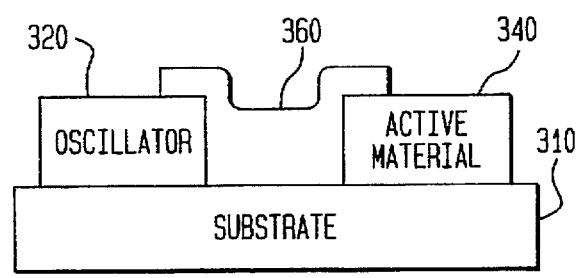
FIG. 3C is a microelectronics model of the chemical sensor shown schematically in FIG. 1C.

Finally, the microelectronics model depicted in FIG. 3C includes a substrate 310 containing, for example, semiconductors such as silicon, germanium, silicon carbide, gallium arsenide, gallium aluminum arsenide, indium phosphide, silicon-on-sapphire (SOS), silicon-on-insulator (SOI), semiconductor alloys, or superconductors such as yttria barium copper oxide (YBCO), other high temperature superconductors and the like, which supports an integrated-circuit oscillator 320 and active material 340 fabricated thereon. Integrated-circuit oscillator 320 is operably coupled to the active material 340 via leads 360. In the preferred embodiment, integrated-circuit oscillator 320, active material 340 and leads 360 are monolithically integrated on the same substrate as shown.

Figure 4A:
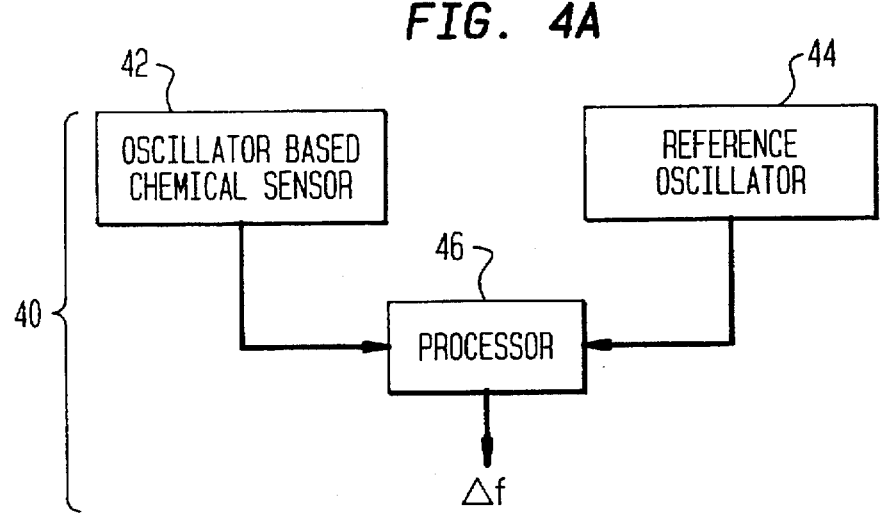
FIG. 4A is a schematic diagram of another embodiment of a chemical sensor of the present invention employing a differential output.

In many applications, the chemical sensor of the present invention will need to measure changes in a sensed condition as opposed to the absolute measurement of the condition. Accordingly, an embodiment of the present invention utilizing a differential output is depicted in the chemical sensor referenced generally by numeral 40 in FIG. 4A. Chemical sensor 40 includes an oscillator-based chemical sensor 42 configured as any of the chemical sensors shown in FIGS. 1A–1C. A reference oscillator 44 having no active material coupled thereto is also provided in close proximity to sensing device 42. Oscillator 44, acting as an oscillator thermometer, is thus subject to the same environmental conditions (i.e., temperature) as chemical sensor 42. The frequency output of chemical sensor 42 and reference oscillator 44 is coupled to, for example, processor 46 capable of generating a frequency difference $\Delta f$ between the frequencies of oscillation of chemical sensor 42 and reference oscillator 44. The frequency difference $\Delta f$ is indicative of changes in the condition sensed by the active layer of chemical sensor 42. That is, sensing device 40 is calibrated so that each $\Delta f$ corresponds to a particular sensed condition.

Figure 4B:
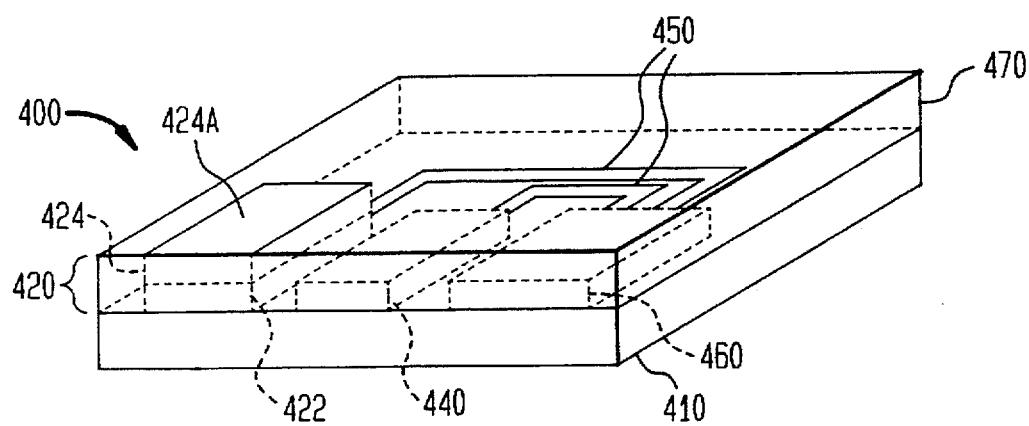
FIG. 4B is a monolithically integrated microelectronics model of the chemical sensor shown schematically in FIG. 4A.

In its preferred embodiment, chemical sensor 40 is fabricated as a monolithically integrated microelectronics package 400 as shown in FIG. 4B. Package 400 includes substrate 410 upon which is fabricated, using microelectronic fabrication techniques, a ring oscillator based chemical sensor 420, a reference ring oscillator 440, a processor 460, and signal coupling paths 450 to operably couple ring oscillator based chemical sensor 420 and reference ring oscillator 440 to processor 460. Ring oscillator based chemical sensor 420 includes at least a ring oscillator portion 422 and an active material portion 424. Signal coupling paths 450 are representative of any structure for coupling the frequency signals of oscillators 422 and 440 to processor 460. For example, paths 450 could denote electrical conductors from oscillators 422 and 440 to processor 460. Paths 450 could also denote telemetry paths from oscillators 422 and 440 to an antenna pickup (not shown) located at processor 460 that is sensitive to the frequency emission of oscillators 422 and 440. Depending on the choice of substrate 410, microelectronics package 400 can also include a passivation layer 470 to chemically isolate all of the elements on substrate 410 from the environment with the exception of a portion 424A of active material 424.

Variations in construction using the teachings of FIG. 3A and FIG. 3B may also be employed in the construction of chemical sensor 420. It is to be understood that the schematic pictorial of FIG. 4B is for conceptual purposes only. In practice, the relative dimensions of ring oscillator based chemical sensor 420 including active material 424, reference ring oscillator 440, and processor 460 are substantially smaller and thinner compared to the substrate. Furthermore, it is understood in practice that ring oscillator portion 422 and any associated analog or digital circuitry comprising processor 460 is formed such that it may contain portions both within and on top of substrate 410. For example, a field-effect transistor which is used in the construction of a ring oscillator can have its source, drain and channel regions of the transistor formed in the substrate, while its gate, gate oxide, metal contacts, sidewall spacers and interlayer dielectrics can be formed on the substrate.

The oscillators used in sensing device 42 or 420 and reference oscillator 44 or 440 are preferably fabricated identically or matched to one another in accordance with methods known in the field of batch fabrication processing of microelectronics. For example, in the case of ring oscillators, a matched pair of ring oscillators has an identical number of inverters and identical gate dimensions so that they have nearly identical frequency characteristics. In this way, common mode rejection of potential interferences is eliminated by the differential output of chemical sensor 40 or processor 460 of microelectronic package 400.

Figure 5:
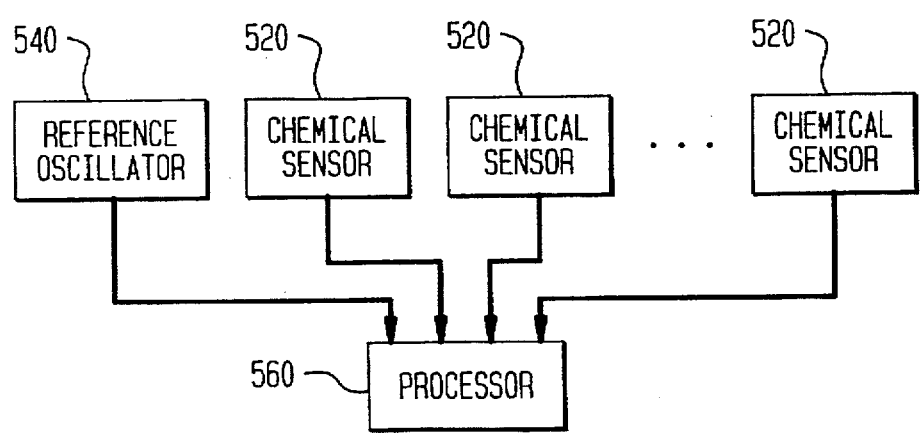
FIG. 5 is a schematic of a construction with a plurality of chemical sensors.

The monolithic integration embodiment of the present invention described above can be extended to form a single package containing a variety of different chemical sensors. That is, a plurality of chemical sensor 420/reference oscillator 440/signal coupling paths 450/processor 460 sets can be provided on a single substrate. Alternately, as schematically shown in FIG. 5, a plurality of chemical sensors 520 and a single reference oscillator 540 may be operably coupled to a single processor 560 by signal coupling paths 550. This is possible because a plurality of oscillator portions can be simultaneously fabricated with different active materials being selected/deposited on each of the oscillator portions for detection of different chemical and/or biological agents. Signal coupling paths 550 may be suitably multiplexed, or each chemical sensor 520 may be selectively interrogated by processor 560 in order to discriminate between different chemical conditions using a single sensor package.

The advantages of the present invention are numerous. One of the main advantages of this class of chemical sensors is the ease of obtaining digital output from the sensor. A digital signal is necessary for processing data from so-called "brilliant sensors". The use of a highly sensitive oscillator eliminates the need for analog-to-digital conversion on-board the chip. Measurement of frequency is extremely accurate and is inherently digital due to pulse counting techniques commonly utilized. For example, measurement of frequency to 1 part in $10^{11}$ over a broad bandwidth is commercially available. Another advantage of the present invention is its ability to function with either bulk or thin film oscillators for chemical detection. Bulk oscillators, such as piezoelectric crystals, can be used as conventionally manufactured and modified to accommodate an active material thereon, or the oscillators can be formed in thin film for monolithic integration.

Another important advantage of the present invention is that it can utilize microelectronics batch processing techniques to fabricate monolithic identical or matched oscillators, for example ring oscillators. Further, the oscillator portion of many chemical sensors can be fabricated with the active material being later selected/deposited to produce a wide variety of different chemical sensors. This will lower the fabrication cost of the ultimate sensing devices for the variety of applications.

Another advantage of one of the embodiments is the use of silicon on sapphire based ring oscillators. Sapphire not only supports the fabrication of high quality microelectronic circuitry, but also has lower thermal conductivity to improve the thermal isolation of the ring oscillator compared with standard semiconductor materials. The chemical resistance and sapphire's resistance to impurity diffusion eliminates the requirement of backside passivation during packaging of the sensors.

Another embodiment within the scope of the present invention is to directly modify the oscillator circuitry itself with an active material. That is, an active metal can be substituted for at least one portion of the electronic interconnection of the circuit. For example, the gate electrode on one or more field effect transistors making up a ring oscillator can be replaced with an active metal material in order to produce a chemical sensor response.

Thus, although the invention has been described relative to specific embodiments thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A chemical sensor comprising:
   a material that changes temperature in response to a chemical condition; and
   a ring oscillator defined by a plurality of microelectronic inverters connected electrically in series, said ring oscillator being coupled to said material to detect the change in temperature in said material wherein a frequency of said ring oscillator changes digitally in correspondence with the change in temperature in said material.

2. A chemical sensor as in claim 1 further comprising a second ring oscillator having the same number of microelectronic inverters as said ring oscillators, each of said microelectronic inverters of said second ring oscillator having the same gate dimensions as those associated with said plurality of microelectronic inverters defining said ring oscillator, said second ring oscillator positioned in proximity to said material wherein a frequency difference between said ring oscillator and said second ring oscillator is indicative of said chemical condition.

3. A chemical sensor as in claim 1 wherein said material is a catalyst in the presence of said chemical condition.

4. A chemical sensor as in claim 1 wherein electrical resistance of said material changes in correspondence with the change in temperature of said material, said chemical sensor further comprising electrical leads for electrically connecting said material with said ring oscillator.

5. A chemical sensor comprising:
   an active material that changes temperature in response to a change in a chemical condition of an environment to which it is exposed;
   a first ring oscillator defined by a first plurality of microelectronic inverters connected electrically in series, said first ring oscillator being coupled to said active material wherein a frequency of said first ring oscillator changes digitally in correspondence with the temperature of said active material;
   a second ring oscillator defined by a second plurality of microelectronic inverters connected electrically in series, said second ring oscillator being matched to said first ring oscillator wherein said second plurality of microelectronic inverters is identical in number and gate dimensions to said first plurality of ring oscillators, said second ring oscillator exposed to said environment in proximity to said active material wherein a frequency of said second ring oscillator changes digitally in correspondence with a temperature of said environment; and
   a processor coupled to said first ring oscillator and said second ring oscillator for generating a frequency difference between said frequency of said first ring oscillator and said frequency of said second ring oscillator, wherein said frequency difference is indicative of said change in said chemical condition.

6. A chemical sensor as in claim 5 wherein said active material is in physical contact with said first ring oscillator.

7. A chemical sensor as in claim 5 further comprising a thermal conduction controller interposed between said active material and said first ring oscillator.

8. A chemical sensor as in claim 5 wherein said material is a catalyst in the presence of said chemical condition.

9. A chemical sensor as in claim 8 wherein electrical resistance of said active material changes in correspondence with the change in temperature of said active material, said chemical sensor further comprising electrical leads for electrically connecting said active material with said first ring oscillator.

10. A monolithically integrated chemical sensor comprising:
    a substrate;
    a first ring oscillator monolithically formed upon said substrate and defined by a plurality of microelectronic inverters connected electrically in series;
    an active material exposed to an environment and capable of participating in a chemical reaction with agents in said environment such that said active material experience a temperature change in response to said chemical reaction, said active material being monolithically formed and operably coupled to said first ring oscillator, wherein a frequency of said first ring oscillator changes digitally in correspondence with said temperature change of said active material;
    a second ring oscillator monolithically formed on said substrate matched to said first ring oscillator in terms of numbers of microelectronic inverters and associated gate dimensions thereof, said second ring oscillator positioned in proximity to said first ring oscillator, wherein a frequency of said second ring oscillator changes digitally in correspondence with the temperature of said environment; and
    a processor monolithically formed on said substrate and coupled to said first ring oscillator and said second ring oscillator for generating a frequency difference between said frequency of said first ring oscillator and said frequency of said second ring oscillator, wherein said frequency difference is indicative of the presence of said agents.

11. A monolithically integrated chemical sensor as in claim 10 wherein said active material is a catalyst in the presence of said chemical reaction.

12. A monolithically integrated chemical sensor as in claim 10 wherein electrical resistance of said active material changes in correspondence with the change in temperature of said active material, said monolithically integrated chemical sensor further comprising electrical leads for electrically connecting said active material with said first ring oscillator.

13. A monolithically integrated chemical sensor as in claim 10 further comprising a plurality of sets of said first ring oscillator and said active material.

14. A monolithically integrated chemical sensor as in claim 13 wherein each said active material is unique for each of said plurality of sets.

15. A chemical sensor comprising:
   a material that changes temperature in response to a chemical condition; and
   a ring oscillator defined by a plurality of microelectronic inverters connected electrically in series, at least one of said plurality of microelectronic inverters being comprised in part by said material wherein a frequency of said ring oscillator changes digitally in correspondence with the change in temperature in said material.

* * * * *

UNITED STATES PATENT AND TRADEMARK OFFICE
CERTIFICATE OF CORRECTION

PATENT NO. : 5,895,629
DATED : April 20, 1999
INVENTOR(S) : Stephen D. Russell et al.

It is certified that error appears in the above-identified patent and that said Letters Patent is hereby corrected as shown below:

Please add the following Assignees:

Science and Technology Corp.
Hampton, Virginia

United States of America as represented by
The Secretary of the Navy
Washington, D.C.

Signed and Sealed this

Twenty-first Day of September, 1999

Attest:

Q. TODD DICKINSON

*Attesting Officer*  *Acting Commissioner of Patents and Trademarks*